United States Patent
Kazakevich et al.

(10) Patent No.: US 8,363,097 B2
(45) Date of Patent: Jan. 29, 2013

(54) ENDOSCOPIC IMAGING SYSTEM

(75) Inventors: Yuri Kazakevich, Andover, MA (US); Tung Van Le, Lawrence, MA (US)

(73) Assignee: Smith & Nephew, Inc., Memphis, TN (US)

(*) Notice: Subject to any disclaimer, the term of this patent is extended or adjusted under 35 U.S.C. 154(b) by 666 days.

(21) Appl. No.: 12/508,162

(22) Filed: Jul. 23, 2009

(65) Prior Publication Data
US 2011/0018988 A1 Jan. 27, 2011

(51) Int. Cl.
*A61B 1/04* (2006.01)

(52) U.S. Cl. .......................................................... 348/68

(58) Field of Classification Search .............. 348/68
See application file for complete search history.

(56) References Cited

U.S. PATENT DOCUMENTS

| | | | |
|---|---|---|---|
| 4,969,450 A | | 11/1990 | Chinnock et al. |
| 5,010,876 A | * | 4/1991 | Henley et al. ............ 600/112 |
| 5,751,341 A | * | 5/1998 | Chaleki et al. .............. 348/65 |
| 5,868,665 A | * | 2/1999 | Biggs ........................ 600/112 |
| 5,879,289 A | | 3/1999 | Yarush et al. |
| 6,092,722 A | | 7/2000 | Heinrichs et al. |
| 6,141,037 A | | 10/2000 | Upton et al. |
| 6,692,431 B2 | * | 2/2004 | Kazakevich ............... 600/178 |
| 6,921,920 B2 | | 7/2005 | Kazakevich |
| 7,289,139 B2 | | 10/2007 | Amling et al. |
| 7,828,721 B2 | * | 11/2010 | Kumei et al. ............... 600/109 |
| 8,029,439 B2 | | 10/2011 | Todd et al. |
| 2003/0050534 A1 | * | 3/2003 | Kazakevich ............... 600/178 |
| 2003/0069475 A1 | | 4/2003 | Banik et al. |
| 2003/0228553 A1 | | 12/2003 | Mandelkern et al. |
| 2004/0264754 A1 | | 12/2004 | Kleen et al. |
| 2005/0099824 A1 | * | 5/2005 | Dowling et al. ............. 362/572 |
| 2006/0111613 A1 | * | 5/2006 | Boutillette et al. ......... 600/136 |
| 2006/0173245 A1 | * | 8/2006 | Todd et al. ................. 600/178 |
| 2006/0178557 A1 | * | 8/2006 | Mintchev et al. ........... 600/104 |
| 2006/0281972 A1 | * | 12/2006 | Pease et al. ................ 600/109 |
| 2007/0030345 A1 | | 2/2007 | Amling et al. |
| 2007/0055104 A1 | * | 3/2007 | Kumei et al. .............. 600/176 |
| 2007/0276183 A1 | | 11/2007 | Melder |
| 2007/0282165 A1 | | 12/2007 | Hopkins et al. |
| 2010/0110168 A1 | * | 5/2010 | Avni et al. ..................... 348/68 |
| 2010/0141744 A1 | | 6/2010 | Amling et al. |
| 2010/0201796 A1 | * | 8/2010 | Chan ............................ 348/68 |
| 2011/0193948 A1 | | 8/2011 | Amling et al. |

FOREIGN PATENT DOCUMENTS

DE 10056438 A1 6/2012

OTHER PUBLICATIONS

International search report and written opinion regarding International patent application PCT/US2010/041927 mailed on Feb. 2, 2012.
Invitation to Pay Additional Fees And, Where Applicable, Protest Fees For PCT/US2010/041927 Dated Sep. 22, 2010.

* cited by examiner

*Primary Examiner* — Tammy Nguyen
*Assistant Examiner* — James Edwards
(74) *Attorney, Agent, or Firm* — Fish & Richardson P.C.

(57) ABSTRACT

An endoscopic imaging system includes an endoscope, a light source assembly coupled to the endoscope that transmits light to the endoscope for illuminating a region of interest, an imaging unit coupled to the light source assembly that receives light through the endoscope reflected from the region of interest, a first power module coupled to the light source assembly that provides electrical power to the light source assembly, and a second and different power module coupled to the imaging unit that provides electrical power to the imaging unit. Other imaging systems and a method are also disclosed.

41 Claims, 7 Drawing Sheets

ENDOSCOPIC IMAGING SYSTEM

BACKGROUND

1. Field of Technology

The present disclosure relates to endoscopic imaging systems.

2. Related Art

Medical endoscopic imaging systems are used in surgical procedures to inspect regions of interest within a patient's body, such as, for example, cavities and joints, through a small incision. In general, an endoscopic imaging system includes an endoscope, a camera head attached to the endoscope, a remote light source tethered to the endoscope via a fiber optic cable, and a camera control unit coupled to the camera head via a power and data cable.

The endoscope includes a rigid or flexible elongated insertion tube that is inserted into the patient's body such that the distal tip of the insertion tube is positioned at the region of interest. The insertion tube defines one or more illumination channel(s) for transmitting light received from the remote light source to the region of interest to illuminate the region of interest. The insertion tube also defines an imaging channel for relaying an image of the region of interest to an image sensor in the camera head.

Typically, for the rigid insertion tube, the illumination channels contain an incoherent fiber optic bundle that extends through the channels, and the imaging channel contains an objective lens followed by one or more rod lenses positioned adjacent to each other in series or a coherent fiber bundle that relays the image formed by the objective lens to the focusing assembly. For the flexible insertion tube, the tube includes an imaging channel that houses an objective lens and a coherent fiber bundle, and one or more illumination channels located adjacent to the imaging channel that house incoherent optical fiber bundles for illumination.

A focusing assembly housed within the endoscope includes optics that can be manipulated by the surgeon to focus the image on the image sensor located in the camera head.

The camera head receives the image of the region of interest from the focusing assembly of the endoscope, converts the image into electronic data, and transmits the data over the power and data cable to the camera control unit for processing. The image is then transmitted by the camera control unit to a display unit that is coupled to the camera control unit. The camera head uses the power and data cable to both receive power and to communicate with the external camera control unit.

SUMMARY

To increase a surgeon's ability to move, rotate, and aim the endoscope of an endoscopic imaging system during a procedure, a cable-free hand-held endoscopic imaging system is desirable. The disclosed endoscopic imaging system includes an endoscope, a light source to transmit light through illumination channels in the endoscope, and an imaging unit to receive images of a region of interest that are formed at a tip of the endoscope that is inserted into the region. The components of the system are freely attachable and detachable from each other.

In an aspect, an endoscopic imaging system includes an endoscope, a light source assembly coupled to the endoscope that transmits light to the endoscope for illuminating a region of interest, an imaging unit coupled to the light source assembly that receives light through the endoscope reflected from the region of interest, a first power module coupled to the light source assembly that provides electrical power to the light source assembly, and a second and different power module coupled to the imaging unit that provides electrical power to the imaging unit.

In an embodiment, the system further includes optics coupled to the light source assembly to enable manipulation of the light to the endoscope for illuminating the region of interest. In another embodiment, the optics enable coupling of light emitted from the light source assembly to the endoscopic. In yet another embodiment, the system further includes an electronic light control circuitry connected to the light source and the imaging unit, wherein the light control circuitry regulates a light output of the light source responsive to control signals from the imaging unit. In a further embodiment, the first power module includes a battery. In yet a further embodiment, the second power module includes a battery.

In an embodiment, the second power module includes an interface for connecting to an external and remote power source via a cable. In another embodiment, the imaging unit is coupled to the light source assembly such that the endoscope, the light source assembly, and the battery are able to rotate together while the imaging unit remains stationary. In yet another embodiment, the second power module includes a battery. In a further embodiment, the second power module includes an interface for connecting to an external and remote power source via a cable. In yet a further embodiment, the system further includes a first coupling means coupling the endoscope to the light source assembly, and a second coupling means coupling the light source assembly to the imaging unit.

In an embodiment, at least one of the first and second coupling means enables detachable coupling. In another embodiment, the second coupling means includes a threaded connector. In yet another embodiment, the light source assembly includes an LED assembly. In a further embodiment, the imaging unit is coupled to the light source assembly such that the endoscope and the light source assembly are able to rotate together while the imaging unit remains stationary. In yet a further embodiment, the system further includes optics located between the endoscope and the imaging unit to enable the imaging unit to receive the light reflected by the region of interest from the endoscope.

In an embodiment, the optics are configured to enable focusing of the image. In another embodiment, the optics are configured to enable zooming into the image. In yet another embodiment, the imaging unit includes a wireless transceiver that receives and transmits control signals and image data representing the image of the region of interest wirelessly from and to an external unit. In a further embodiment, the external unit to which the wireless transceiver is wirelessly coupled is a camera control unit that transmits the control signals to the imaging unit; receives the image data from the imaging unit; and causes a display unit coupled to the camera control unit to display the image represented by the image data.

In another aspect, an endoscopic imaging system includes an endoscope having a front end for viewing a region OF interest, a light source assembly that transmits light to the endoscope for illuminating the region of interest, a first coupling means coupling the endoscope to the light source assembly, an imaging unit that receives an image of the region of the interest formed by the endoscope, and a second coupling means coupling the light source assembly to the imaging unit, wherein at least one of the first and second coupling means enables detachable coupling.

In an embodiment, the second coupling means includes a threaded connector. In another embodiment, the system further includes optics coupled to the light source assembly to enable manipulation of the light to the endoscope for illuminating the region of interest. In yet another embodiment, the optics enable coupling of light emitted from the light source assembly to the endoscope. In a further embodiment, the system further includes an electronic light control circuitry connected to the light source and the imaging unit wherein the light control circuitry regulates a light output of the light source responsive to control signals from the imaging unit. In yet a further embodiment, the light source assembly includes an LED assembly.

In an embodiment, the imaging unit is coupled to the light source assembly such that the endoscope and the light source assembly are able to rotate together while the imaging unit remains stationary. In another embodiment, the system further includes optics located between the endoscope and the imaging unit to enable the imaging unit to receive the light reflected by the region of interest from the endoscope. In yet another embodiment, the optics are configured to enable focusing of the image. In a further embodiment, the optics are configured to enable zooming into the image. In yet a further embodiment, the imaging unit includes a wireless transceiver that receives and transmits control signals and image data representing the image of the region of interest wirelessly from and to an external unit.

In an embodiment, the external unit to which the wireless transceiver is wirelessly coupled is a camera control unit that transmits the control signals to the imaging unit; receives the image data from the imaging unit; and causes a display unit coupled to the camera control unit to display the image represented by the image data. In another embodiment, the second coupling means enables detachable coupling of the light source assembly to the imaging unit. In yet another embodiment, the system further includes a power module coupled to the imaging unit to provide electrical power to the imaging unit and the light source assembly. In a further embodiment, the system further includes an electrical contact mechanism coupled to the imaging unit and the light source assembly, the electrical contact mechanism being connected to the power module to transmit electrical power provided by the power module to the light source assembly.

In an embodiment, the first coupling means enables detachable coupling of the endoscope to the light source assembly. In another embodiment, the imaging unit includes a cable over which the imaging unit receives and transmits control signals and image data representing the image of the region of interest from and to an external unit. In yet another embodiment, the imaging unit further receives power from an external power unit through the cable. In a further embodiment, the endoscope includes a light post configured to be received by the light source assembly, the light post having a central longitudinal axis that is parallel to an optical axis of the system.

In yet another aspect, an endoscopic imaging system includes an endoscope, a light source assembly coupled to the endoscope that transmits light to the endoscope for illuminating a region of interest, an imaging unit coupled to the light source assembly that receives light through the endoscope reflected from the region of interest, wherein the imaging unit includes a wireless transceiver that receives and transmits control signals and image data representing the image of the region of interest wirelessly from and to an external unit, wherein the imaging unit is coupled to the light source assembly such that the endoscope and the light source assembly are able to rotate together while the imaging unit remains stationary.

In an embodiment, the system further includes optics coupled to the light source assembly to enable manipulation of the light to the endoscope for illuminating the region of interest. In another embodiment, the optics enable coupling of light emitted from the light source assembly to the endoscope. In another embodiment, the system further includes an electronic light control circuitry connected to the light source and the imaging unit wherein the light control circuitry regulates a light output of the light source responsive to control signals from the imaging unit. In yet another embodiment, the light source assembly includes an LED assembly. In a further embodiment, the system further includes optics located between the endoscope and the imaging unit to enable the imaging unit to receive the light reflected by the region of interest from the endoscope. In yet a further embodiment, the optics are configured to enable focusing of the image.

In an embodiment, the optics are configured to enable zooming into the image. In another embodiment, the external unit to which the wireless transceiver is wirelessly coupled is a camera control unit that transmits the control signals to the imaging unit; receives the image data from the imaging unit; and causes a display unit coupled to the camera control unit to display the image represented by the image data. In another embodiment, the system further includes a power module coupled to the imaging unit to provide electrical power to the imaging unit and the light source assembly. In yet another embodiment, the system further includes an electrical contact mechanism coupled to the imaging unit and the light source assembly, the electrical contact mechanism being connected to the power module to transmit electrical power provided by the power module to the light source assembly. In a further embodiment, the imaging unit includes a cable over which the imaging unit receives and transmits control signals and image data representing the image of the region of interest from and to an external unit. In yet a further embodiment, the imaging unit further receives power from an external power unit through the cable.

In a further aspect, an imaging system includes an endoscope; a light emitting diode (LED) assembly coupled to the endoscope that provides light to be directed to a region of interest by the endoscope; an electronic control circuitry operatively coupled to the LED assembly that regulates output of the light provided by the LED assembly based on received control signals; and an imaging unit comprising an image sensor and coupled to the LED assembly. In an embodiment, the electronic control circuitry regulates a drive current provided to the LED assembly to regulate an intensity of light emitted by the LED assembly responsive to a brightness of the region of interest detected by the image sensor. In another embodiment, the electronic control circuitry is configured to synchronize a duty cycle of the LED assembly with a frame clock of the image sensor; and change the duty cycle of the LED assembly responsive to a brightness of the region of interest detected by the image sensor.

In yet a further aspect, a method includes coupling an endoscope to a first coupling means that is coupled to a light source such that light provided by the light source is transmitted through the endoscope to a region of interest, coupling an imaging unit to a second coupling means that is coupled to the light source of the unit to form an endoscopic imaging system, the imaging unit being coupled to the light source such that an image formed by the endoscopic is received by the imaging unit, and coupling a power module to the unit, the power module providing electrical power to the endoscopic imaging system, wherein at least one of the first and second coupling means enables detachable coupling.

In an embodiment, the light source includes an LED assembly. In another embodiment, coupling the power module includes coupling a power module that provides electrical power to the imaging unit and to the light source. In yet another embodiment, coupling the imaging unit to the second coupling means that is coupled to the light source includes coupling the imaging unit such that an electrical contact mechanism is coupled to the imaging unit and the light source, the electrical contact mechanism being connected to the power module to transmit electrical power provided by the power module to the light source. In a further embodiment, the first coupling means permits the light source and the endoscope to rotate together while the imaging unit remains stationary. In yet a further embodiment, the method further includes controlling a duty cycle of the LED assembly to regulate a light output responsive to a brightness of the region of interest received by the imaging unit. In an embodiment, the method further includes regulating a drive current provided to the LED assembly to regulate an intensity of light emitted by the LED assembly responsive to a brightness of the region of interest received by the imaging unit.

Further areas of applicability of the present disclosure will become apparent from the detailed description provided hereinafter. It should be understood that the detailed description and specific examples, while indicating the preferred embodiment or the disclosure, are intended for purposes of illustration only and are not intended to limit the scope of the disclosure.

BRIEF DESCRIPTION OF THE DRAWINGS

The accompanying drawings, which are incorporated in and form a part of the specification, illustrate the embodiments of the present disclosure and together with the written description serve to explain the principles, characteristics, and features of the disclosure. In the drawings.

DETAILED DESCRIPTION OF THE EMBODIMENTS

The following description of the preferred embodiment(s) is merely exemplary in nature and is in no way intended to limit the disclosure, its application, or uses.

Figure 1:
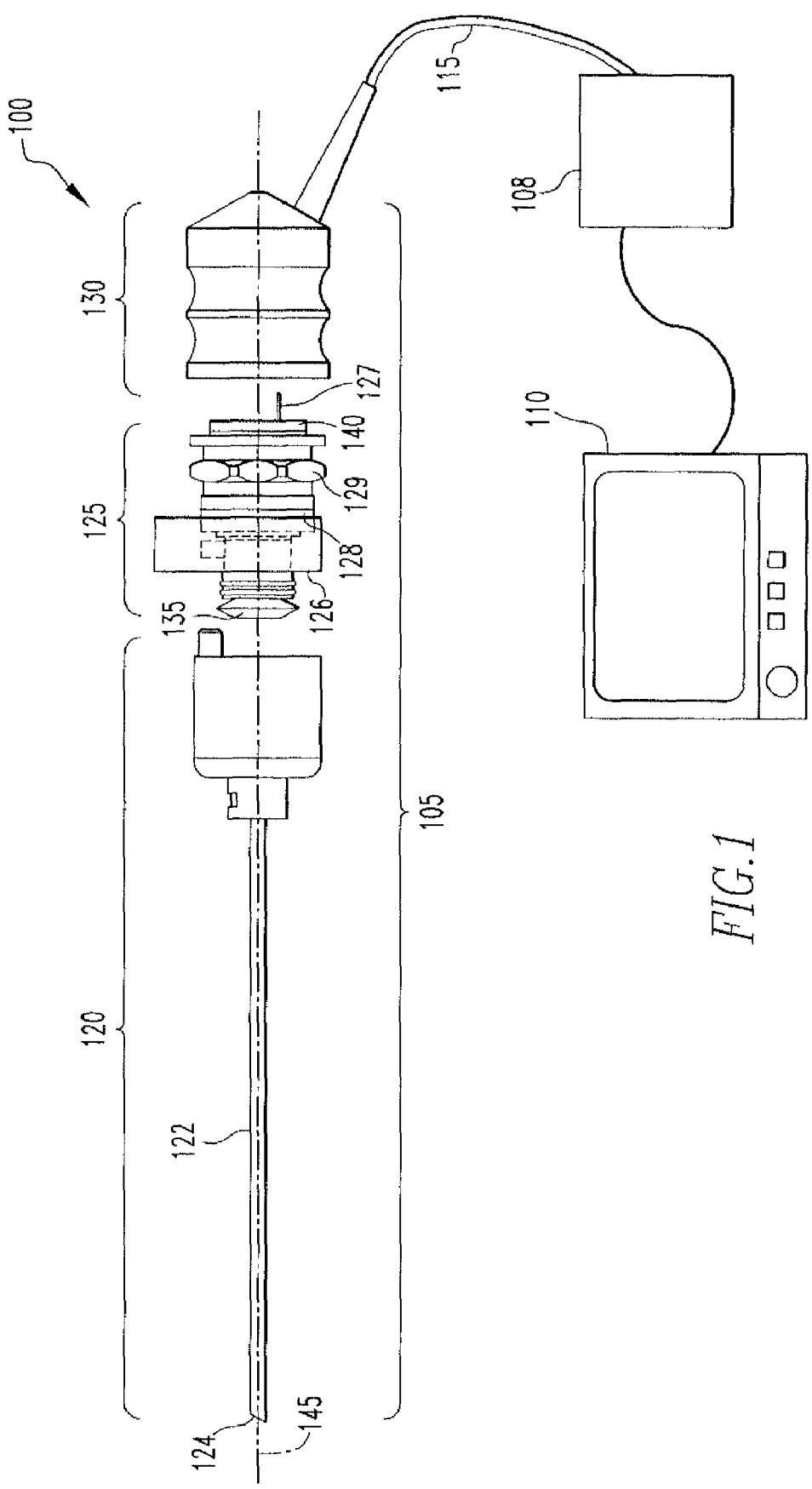
FIG. 1 illustrates components of a first implementation of an endoscopic imaging system.
Figure 2:
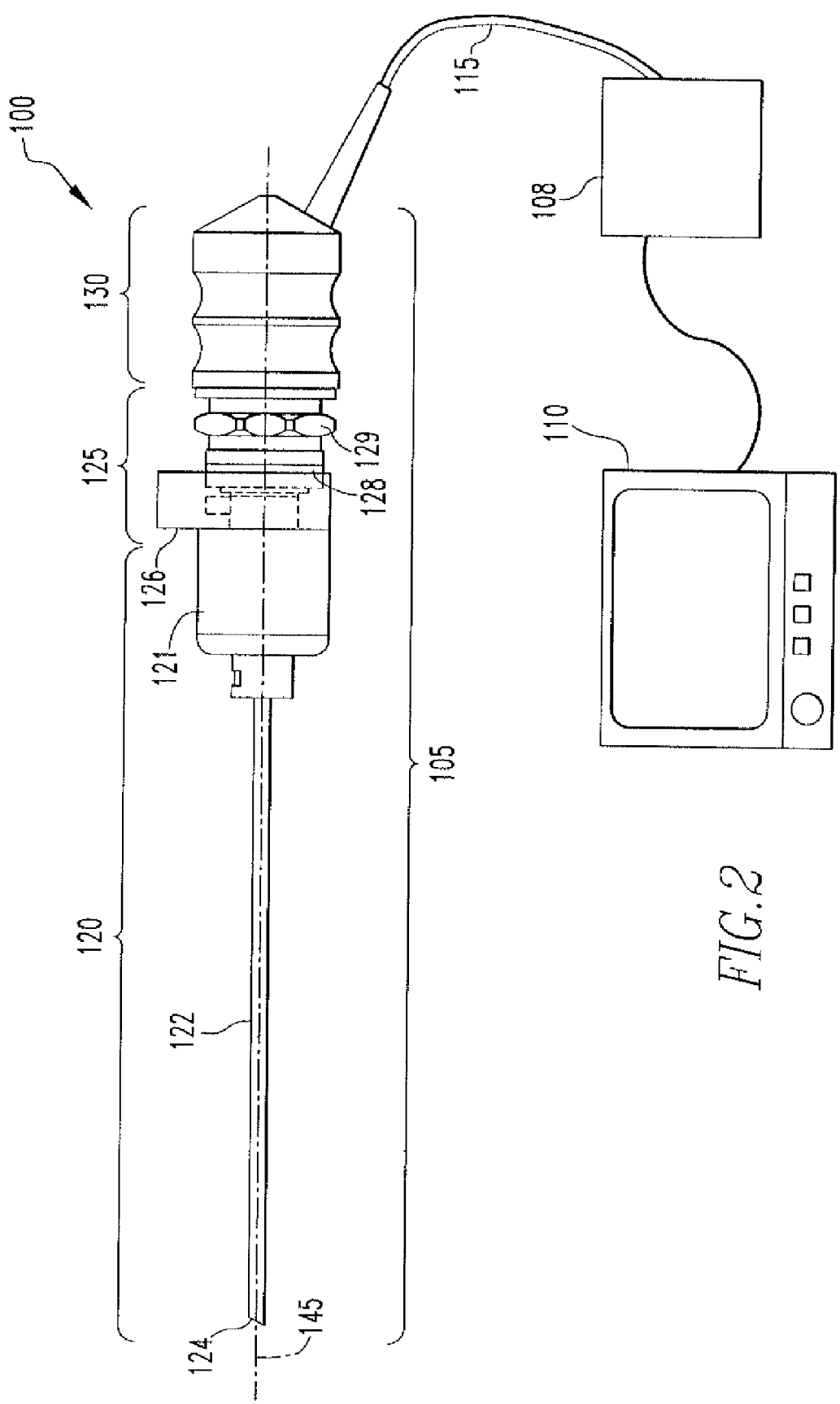
FIG. 2 shows the endoscopic imaging system of FIG. 1, assembled.

Referring to FIGS. 1 and 2, an endoscopic imaging system 100 includes a hand-held unit 105 tethered to a camera control unit 108 by a cable 115. The hand-held unit 105 includes three components: an endoscope 120, an LED endocoupler 125, and an imaging unit 130. The three components are freely attachable to and detachable from each other via respective coupling means 135 and 140. The ability to disassemble the hand-held unit 105 of the endoscopic imaging system 100 into its three components adds versatility to the system 100 in that the components of the hand-held unit 105 are individually replaceable. For example, different endoscopes 120, for example, 30° direction of view endoscopes, 70° direction of view endoscopes, endoscopes of various diameters, rigid or flexible, and the like, can be coupled to the LED endocoupler 125. Similarly, different LED endocouplers 125 having various focal lengths may be coupled to the imaging units 130. Also, different imaging units 130 may be utilized.

Moreover, the ability to disassemble the hand-held unit 105 also facilitates repair of the system 100 by allowing separate removal and repair of each component. Although modularity of the device is preferred, it is not necessary. For example, the endoscope 120 and the LED endocoupler 125 can be one assembly that is not detachable, the imaging unit 130 and the LED endocoupler 125 can be one assembly that is not detachable, or all three components can be one assembly that is not detachable. Furthermore, the imaging unit 130 can be shaped as a handle, for example, either as an in-line handle or a pistol grip handle. In addition, it is possible to have a handle whereby the device includes a handle that houses the LED and the focusing assembly in a fixed position, i.e., the LED and the focusing assembly are integral, whereby a focusing ring is not necessary.

Figure 3:
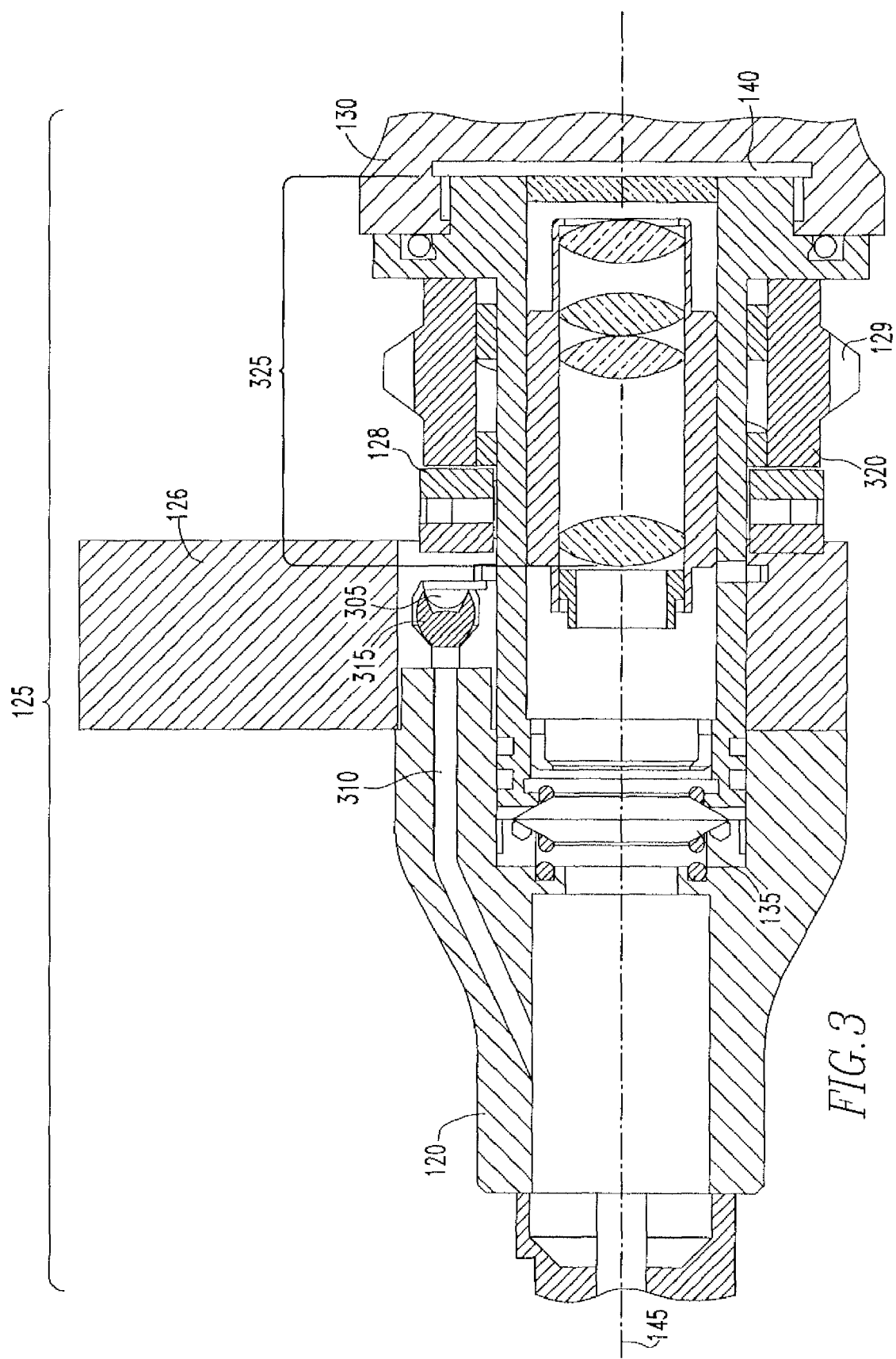
FIG. 3 is a cross-sectional view of an LED endocoupler of the endoscopic imaging system of FIG. 1.

Referring also to FIGS. 2 and 3, the endoscope 120 includes a proximal housing 121, and an insertion tube 122 having an angled distal tip 124. The proximal housing 121 and the insertion tube 122 house a fiber optic bundle 310. The endoscope 120 receives light from the LED endocoupler 125 and transmits the light via the fiber optic bundle 310 to a region of interest to illuminate the region of interest. An optical image is formed by an objective lens (not shown) at the distal tip 124. The insertion tube 122 contains one or more rod lenses (not shown) that relay the optical image of the region of interest formed by the objective lens. Alternatively, rather than rod lenses, the insertion tube 122 can contain a coherent fiber bundle, in which case the insertion portion can be flexible.

The LED endocoupler 125 is attached to the endoscope 120 via the coupling means 135, for example, a snap-fit connector, and is attached to the imaging unit 130 via the coupling means 140, for example, a threaded C-mount connector. The LED endocoupler 125 includes an LED assembly having one or more light emitting diodes (LEDs) for transmitting light to the region of interest through the endoscope 120, such as described in U.S. Pat. No. 6,921,920 entitled "Solid-state light source", and U.S. Pat. No. 6,692,431 entitled "Endoscopic system with a solid-state light source," the contents of both being incorporated herein by reference in their entirety. As shown in FIG. 3, the LED assembly 305 is coupled to the fiber optic bundle 310 through an optical coupling device 315, for example, a Total Internal Reflection (TIR) type optical coupling device. Such coupling devices can be commercially obtained, for example, from FRAEN Corporation (Reading, Mass.). The LED endocoupler 125 also includes a rotational joint 128 such as described in U.S. Pat. No. 6,692,431 that allows the LED assembly 305 of LED endocoupler 125 and the endoscope 120 to rotate together as a unit about axis 145, via the use of rotation handle 126, relative to the remainder of LED endocoupler 125 and imaging unit 130. Axis 145 is, for example, the optical axis of the endoscopic imaging system 100.

The LED endocoupler 125 receives electrical power from the imaging unit 130 through electrical contact 127 (FIG. 1). Electrical power is provided to the LED assembly 305 by an electrical connection (not shown) through the rotational joint 128 such as described in U.S. Pat. No. 6,692,431.

The LED endocoupler 125 further includes a focusing assembly 320 composed of a focusing ring 129 and the focusing lenses 325. A user can manually rotate the focusing ring 129 to bring the image, that is formed at the distal end 124 of the scope and relayed to the image sensor located in the camera head, into focus on the sensor.

The imaging unit 130 includes an image sensor (not shown), for example, a charge coupled device sensor or a CMOS sensor, that receives the focused image from the focusing lenses 325 of the LED endocoupler 125 and that converts the focused image into electronic image data. The imaging unit 130 transmits the image data via cable 115 to the camera control unit 108 for processing and subsequent transmission of the image to the display unit 110. The imaging unit 130 also receives control signals and power from the camera control unit 108 over the cable 115.

The imaging unit 130 may also include button switches (not shown) to provide a user interface for controlling of various functions, e.g. taking a still image, operating a video recorder, adjusting image brightness, etc.

The camera control unit 108 includes a user interface that allows the user of the system 100 to control the operation of the imaging unit 130 and to perform various processing of the image data received from the imaging unit 130. The display unit 110 displays the image data as an image on a monitor for viewing by the user.

In use, a surgeon or other medical personnel selects an endoscope 120 and an LED endocoupler 125 with the appropriate focal length and assembles the hand-held unit 105 by attaching the selected endoscope 120 to the LED endocoupler 125 and attaching the imaging unit 130 to the LED endocoupler 125. After assembling the hand-held unit 105 and verifying that the hand-held unit 105 is properly connected to the camera control unit 108 by the cable 115, the surgeon guides the distal tip 124 of the endoscope 120 to the region of interest. To change the effective field of view of the endoscope 120, the surgeon rotates the endoscope 120 by rotating the LED endocoupler 125 using the rotation handle 126. The rotating joint 128 enables the combination of the endoscope 120 and the LED assembly (hereinafter referred to as "the endoscope-LED assembly unit") to rotate without changing the orientation of the image on the image sensor. Separate from rotating the endoscope-LED assembly unit, the surgeon can focus the image relayed through the endoscope 120 by using the focusing ring 129. In particular, the surgeon views the images on the display unit 110 and rotates the focusing ring 129 as necessary to adjust the displayed image. Similar to the coupler 125 and the endoscope 120, the imaging unit 130 may be interchangeable. In addition, the coupler may include a zoom feature that can be controlled by a separate ring.

Figure 4:
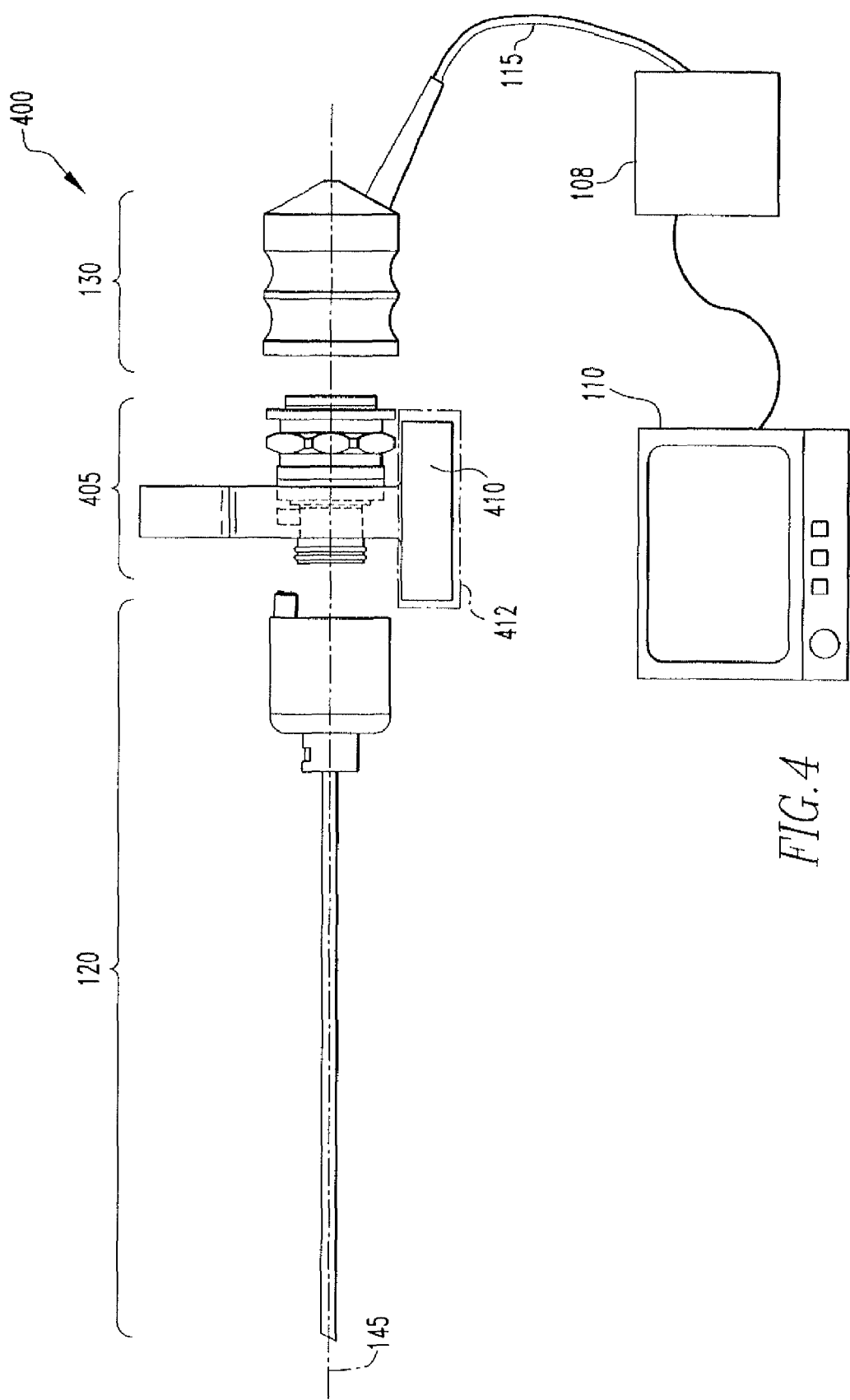
FIG. 4 illustrates components of a second implementation of an endoscopic imaging system.

Referring to FIG. 4, an endoscopic imaging system 400 includes an endoscope 120, an imaging unit 130, an LED endocoupler 405 coupled to the endoscope 120 and to the imaging unit 130 via respective coupling means, and a battery module 410 attached to the LED endocoupler 405 to provide electric power to the LED endocoupler 405. The battery mobile 410 includes a battery (not shown) that can be either rechargeable or single-use and is received in a housing 412 of the module 410. The housing 412 closes in a water-tight sealed fashion, for example, using a cap or clam-shell design. The battery module 410 includes power management circuitry for conserving the battery power and using battery power in an efficient way.

Because the LED endocoupler 405 receives electric power from the battery module 410, in this implementation, the LED endocoupler 405 does not include an electrical contact, such as the electrical contact 127 shown in FIG. 1. As in the system 100 of FIG. 1, the imaging unit 130 of system 400 is coupled to a camera control unit 108 through the cable 115. The imaging unit 130 receives control, transmission, and power signals from the camera control unit 108. However, the imaging unit 108 does not transmit power signals to the LED endocoupler 405.

A particular advantage of system 400 is that it is fully backward compatible with commercially available camera heads (imaging units) because the electrical power to the LED endocoupler 405 is provided by the battery module 410, and no changes to the imaging unit 130 are required to enable power transmission from the imaging unit 130 to the LED endocoupler 405.

As in the LED endocoupler 125, the LED endocoupler 405 includes a rotational joint (not shown) that allows the LED assembly 305 (FIG. 3) of LED endocoupler 405, the battery module 410 and the endoscope 120 to rotate together as a unit about axis 145 relative to the remainder of LED endocoupler 405 and imaging unit 130. The advantage of such a configuration is that the battery module 410 and the LED assembly in the LED endocoupler 405 move in unison. As a result, the connection between the battery module 410 and the LED assembly is simplified, for example, negating the need for a slip-ring type or other dynamic connections.

Figure 5:
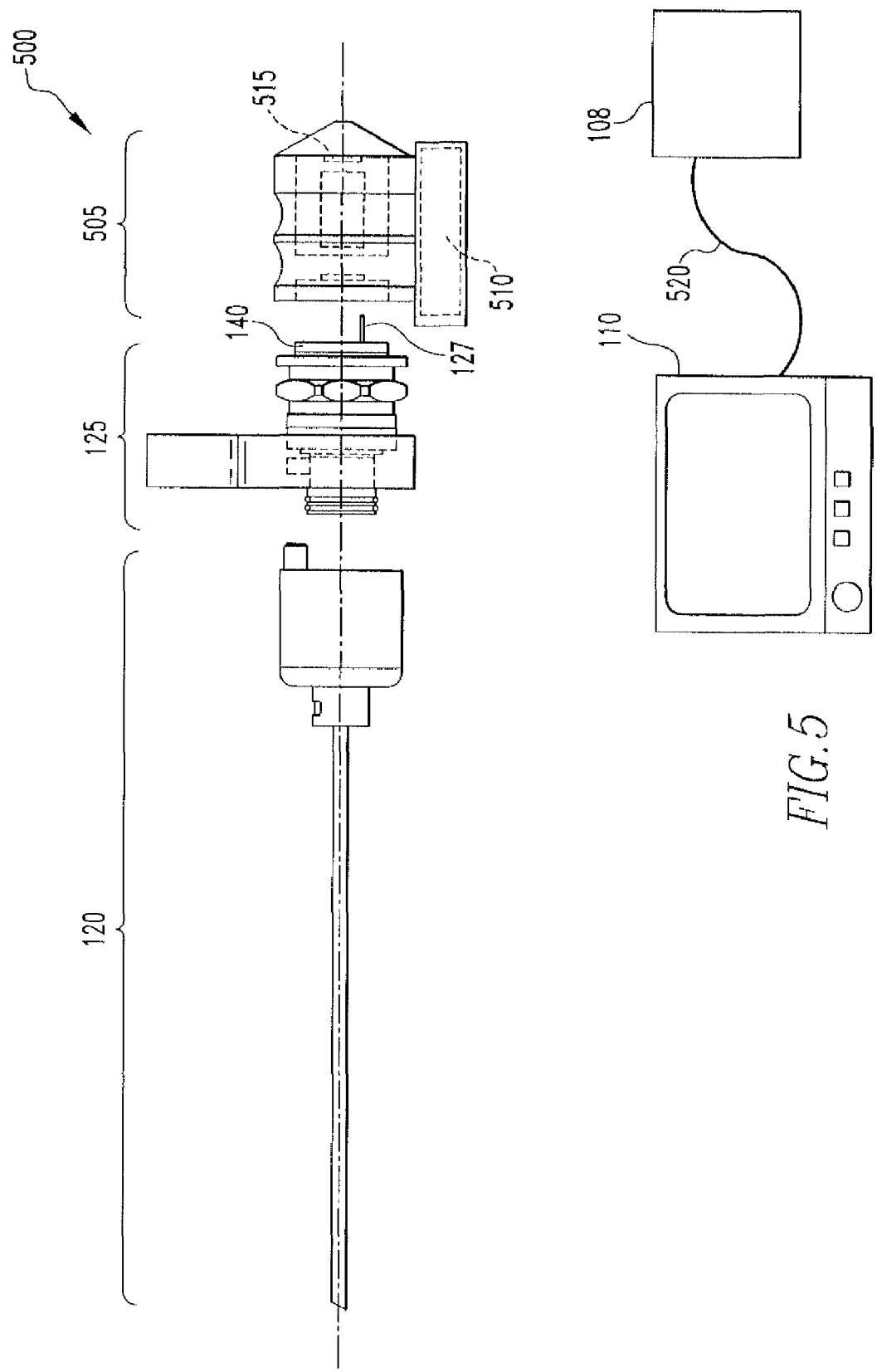
FIG. 5 illustrates components of a third implementation of an endoscopic imaging system.

Referring to FIG. 5, an endoscopic imaging system 500 includes an endoscope 120, an LED endocoupler 125 coupled to endoscope 120 via a coupling means (not shown), and an imaging unit 505 that is attached to the LED endocoupler 125 via a coupling means 140. Imaging unit 505 includes a battery module 510 and a wireless transceiver module 515. The battery module 510 can include a battery, a housing to receive the battery, and power management circuitry as described above with reference to the battery module 410. The battery module 510 provides electric power to both the imaging unit 505 and the LED endocoupler 125. To provide power to the LED endocoupler 125, the system 100 includes an electrical contact 127, similar to the electrical contact 127 of FIG. 1.

Figure 6:
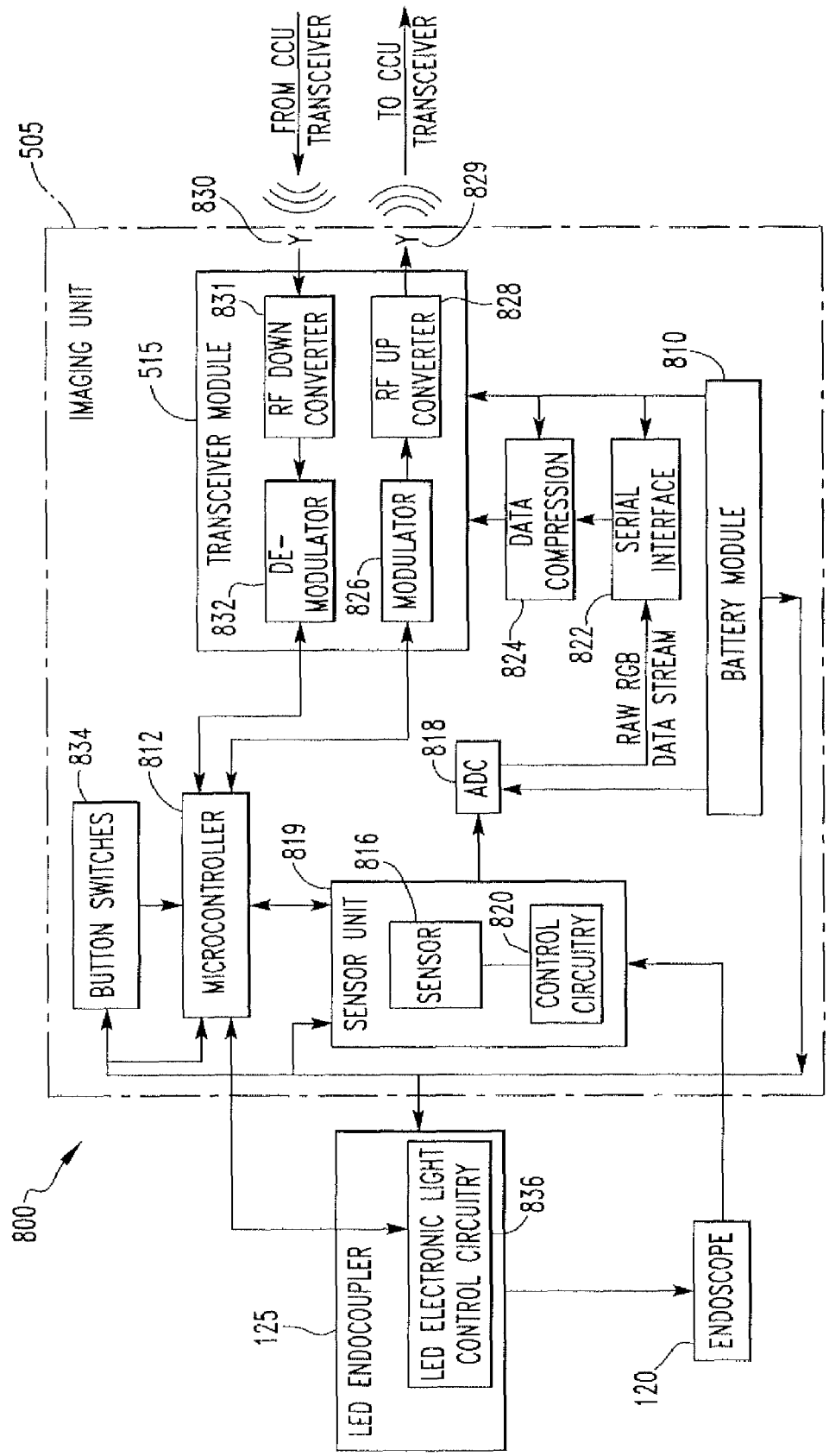
FIG. 6 shows a block diagram of an endoscopic imaging system, including a wireless transceiver module.

The LED endocoupler 125 includes an LED electronic light control circuitry 836 (FIG. 6) to control the operation of the one or more LEDs in the LED endocoupler. In some implementations, the electronic light control circuitry can regulate the brightness of the light emitted by the LEDs by regulating the duty cycle of the LEDs or the drive current of the LEDs via an image sensor feedback loop. This implementation is discussed in greater detail below.

The wireless transceiver module 515 includes a wireless transmitter/receiver and accompanying interface circuitry. Such transceivers may be commercially obtained from Amimon (Herzlia, Israel). The wireless transceiver module 515 transmits and receives control and image data to and from the camera control unit 108 wirelessly. The camera control unit 108 is coupled to a display unit 110 via cable 520 to display images received from the endoscopic imaging system 500. To minimize time lag between acquisition of the image and display on the display unit 110, the transceiver must have the ability to receive and transmit wide signal bandwidth. In operation, a surgeon performs a procedure using the endoscopic imaging system 500 while looking at the display unit 110. The use of a wide signal bandwidth capable wireless transceiver module 515 provides image streams in real-time without latency of image display so that the dexterity and surgical precision are not adversely affected.

The wireless transceiver module 515 receives and transmits image data to and from the camera control unit 108 by RF modulation. A configuration of a wireless endoscopic system 800 (FIG. 6) includes an endoscope 120, an LED endocoupler 125, and an imaging unit 505. The sensor unit 819 of the imaging unit 505 includes image sensor 816 and its control circuitry 820. The image sensor 816 receives the image of the region of interest, and converts the optical image data into electrical signals. The electrical signals are converted into digital format, via an analog-digital convertor (ADC) 818. The digital signals are sent to a serial interface 822 where the signals are serialized (or further processing. In some sensors, such as a system on a chip design, the ADC 818 and/or serial interface 822 may be integrated into the sensor. In other implementations, the ADC 818 and/or serial interface 822 are external to the sensor. The serialized signals are optionally compressed via data compression circuitry 824. The signals are then sent to a wireless transceiver module 515 that modulates the signals, via a modulator 826, and performs RF up conversion, via an RF up convertor 828, thereby creating a signal suitable for wireless transmission, via antenna 829, to a wireless transceiver (not shown) in the camera control unit 108.

In addition, the wireless transceiver module 515 receives control signals from the camera control unit 108 to control one or more components of the system 800 and ensure reliability of a wireless link by providing a closed loop feedback between the camera control unit 108 and the imaging unit 505. The wirelessly transmitted control signals from the camera control unit 108 are received by antenna 830 and converted into digital electrical signals by RF down converter 831 and demodulator 832.

A micro-controller 812, located within the imaging unit 505, establishes and controls communication between the camera control unit 108 (via transceiver module 515) and both the sensor unit 819 and LED electronic light control circuitry 836. In many endoscopic imaging systems, the imaging unit 505 includes one or more switches 834, e.g. operated by buttons or other means of user interface, that allow the operating surgeon to control the most frequently used functions, such as taking a picture, operation of a recording device, etc, from the handheld portion of the system. The commands sent by the switches 834 are processed by the micro-controller 812 and are sent to the proper element of the system for activating the desired function of the element.

To provide electrical power to the individual components of the system 800 including the LED endocoupler 125 and the imaging unit 505, the system 800 includes a power module 810, eg battery or other power means. As mentioned above, the camera control unit 108 contains a transceiver module, similar to transceiver module 515. Both transceiver modules, in aggregate, establish the closed loop wireless link between the imaging unit 505 and the camera control unit 108.

Figure 7:
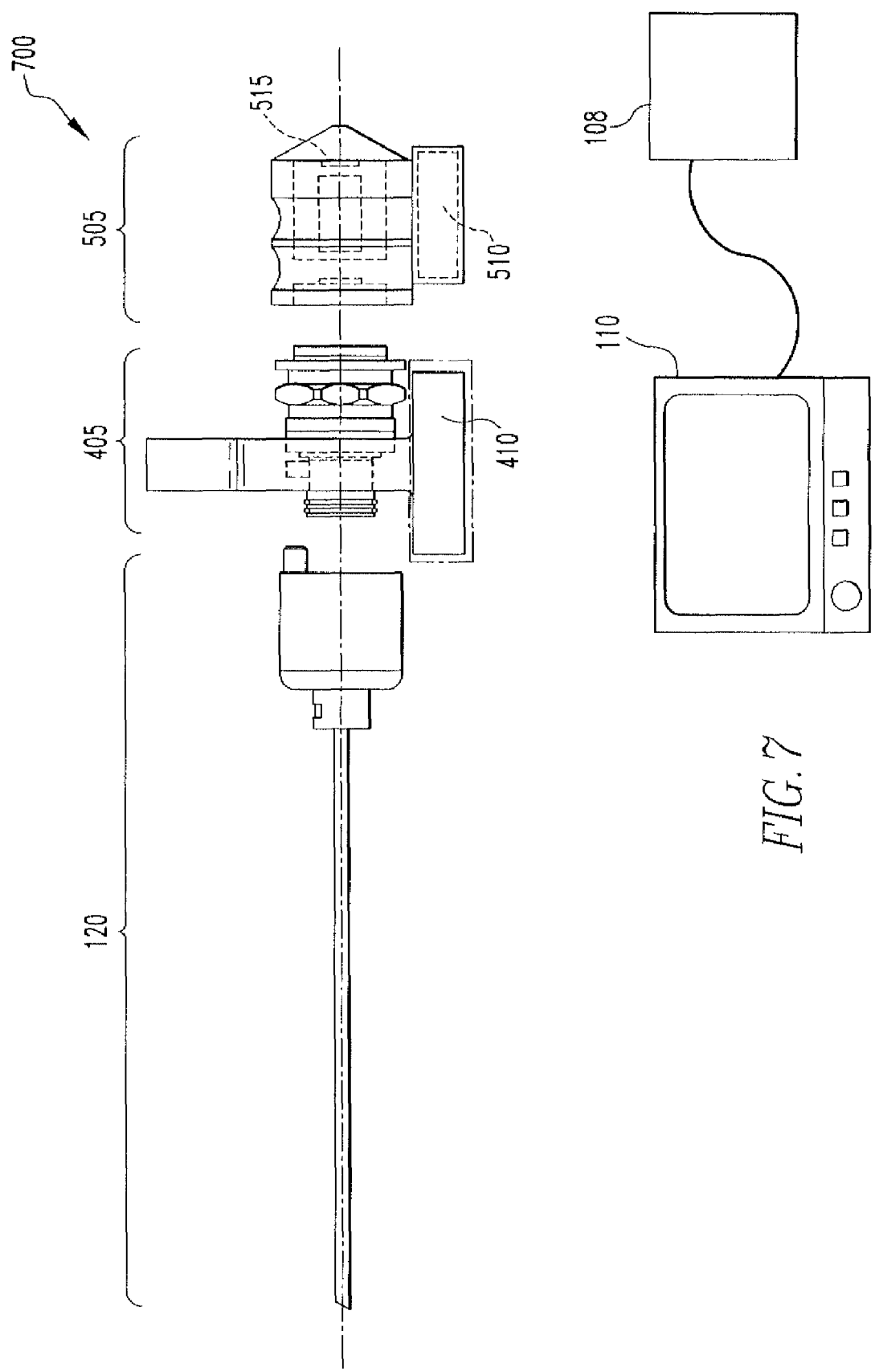
FIG. 7 illustrates components of a fourth implementation of an endoscopic imaging system.

In another implementation, both the LED endocoupler 125 and the wireless transceiver module 515 can receive power from dedicated power sources. Referring to FIG. 7, an endoscopic imaging system 700 includes a first battery module 410 attached to the LED endocoupler 405, and a second, different battery module 510 attached to the imaging unit 505 to provide electrical power to the components of the system 700. In such an implementation, because each unit of the endoscopic imaging system has its own power source, an electrical contact between the LED endocoupler 125 and the imaging unit 130 is not required.

Other implementations are within the scope of the claims. For example, more than one LIED can be used in the LED assembly 305 to provide illumination. In such an implementation, the fiber bundle in the endoscope 120 can be split into multiple bundles. The distal end of the LED endocoupler 125 in which the LED assembly 305 is located can receive multiple terminated fiber bundles corresponding to multiple LEDs at the receiving end of the coupling means 135 that couples the LED endocoupler 125 to the endoscope 120. When the LED endocoupler 125 is attached to the coupling means 135, the LED endocoupler 125 is locked in place such that the terminated end of the fiber bundle aligns with the coupling means 135 and directs the LED light energy into the illumination channel of the endoscope 120. Alternatively, a coupling means can be located at the proximal end of the endoscope 120, aligned with and permanently fixed to the fiber bundle face. When the endoscope 120 is connected to the LED endocoupler 125, the proximal end of the coupling means is mechanically aligned with the LED and provides for channeling the light energy into the illumination channel of the endoscope 120.

The endoscopic imaging system 100 can include an electronic light control unit (e.g., electronic light control circuitry 836) that regulates a brightness of the light emitted by the LED assembly based on control signals, for example, by regulating the duty cycle of the LEDs or the drive current of the LEDs in the LED assembly. Adjusting the duty cycle of the LEDs enables adjusting the brightness of the light emitted by the LED assembly. For example, the LEDs in the LED assembly can be synchronized with the frame/field clock of the sensor unit 819 in the imaging unit 505. Subsequently, the LED duty cycle per image frame (or field) can be dynamically adjusted via an image sensor feedback loop. This can allow the optimal use of the LED assembly, which can be enabled only for the time that is necessary for adequate illumination of the region being imaged. Alternatively, the adjustment of the brightness of the LED can be dynamically controlled using a similar feedback loop for adjusting the LED drive current. As the region being imaged becomes brighter, the current through the LED is automatically reduced, thereby dimming the light output. In another implementation, a combination of duty cycle and drive current adjustment can be employed to regulate the brightness of the light emitted by the LED assembly.

In addition, rather than being located in the camera head, the sensor may be located at the distal tip of the scope or anywhere along the endoscope.

As various modifications could be made to the exemplary embodiments, as described above with reference to the corresponding illustrations, without departing from the scope of the disclosure, it is intended that all matter contained in the foregoing description and shown in the accompanying drawings shall be interpreted as illustrative rather than limiting. Thus, the breadth and scope of the present disclosure should not be limited by any of the above-described exemplary embodiments, but should be defined only in accordance with the following claims appended hereto and their equivalents.

What is claimed is:

1. An endoscopic imaging system comprising:
    an endoscope having a front end for viewing a region of interest;
    a light source assembly that transmits light to the endoscope for illuminating the region of interest;
    a first coupling means coupling the endoscope to the light source assembly such that the endoscope is rotationally stationary with respect to the light source assembly and the endoscope is freely attachable to and detachable from the light source assembly;
    an imaging unit that receives an image of the region of the interest formed by the endoscope; and
    a second coupling means coupling the light source assembly to the imaging unit such that the light source assembly is freely attachable to and detachable from the imaging unit, wherein the light source assembly includes a rotational joint that allows the light source assembly and the endoscope to rotate together while the imaging unit remains stationary.

2. The system of claim 1 comprising:
a first power module coupled to the light source assembly that provides electrical power to the light source assembly; and
a second and different power module coupled to the imaging unit that provides electrical power to the imaging unit.

3. The system of claim 2, wherein the second power module comprises an interface for connecting to an external and remote power source via a cable.

4. The system of claim 2, wherein the first power module comprises a battery.

5. The system of claim 4, wherein the second power module comprises a battery.

6. The system of claim 4, wherein the second power module comprises an interface for connecting to an external and remote power source via a cable.

7. The system of claim 4, wherein the imaging unit is coupled to the light source assembly such that the endoscope, the light source assembly, and the battery are able to rotate together while the imaging unit remains stationary.

8. The system of claim 2, wherein the second power module comprises a battery.

9. The system of claim 1, wherein the second coupling means comprises a threaded connector.

10. The system of claim 1, further comprising optics coupled to the light source assembly to enable manipulation of the light to the endoscope for illuminating the region of interest.

11. The system of claim 10, wherein the optics enable coupling of light emitted from the light source assembly to the endoscope.

12. The system of claim 1, further comprising an electronic light control circuitry connected to the light source and the imaging unit wherein said light control circuitry regulates a light output of the light source responsive to control signals from the imaging unit.

13. The system of claim 1, wherein the light source assembly comprises an LED assembly.

14. The system of claim 1, further comprising optics located between the endoscope and the imaging unit to enable the imaging unit to receive the light reflected by the region of interest from the endoscope.

15. The system of claim 14 wherein the optics are configured to enable focusing of the image.

16. The system of claim 14, wherein the optics are configured to enable zooming into the image.

17. The system of claim 1 wherein the imaging unit comprises a wireless transceiver that receives and transmits control signals and image data representing the image or the region of interest wirelessly from and to an external unit.

18. The system of claim 17, wherein the external unit to which the wireless transceiver is wirelessly coupled is a camera control unit that:
transmits the control signals to the imaging unit;
receives the image data from the imaging unit; and
causes a display unit coupled to the camera control unit to display the image represented by the image data.

19. The system of claim 1, further comprising a power module coupled to the imaging unit to provide electrical power to the imaging unit and the light source assembly.

20. The system of claim 19, further comprising an electrical contact mechanism coupled to the imaging unit and the light source assembly, the electrical contact mechanism being connected to the power module to transmit electrical power provided by the power module to the light source assembly.

21. The system of claim 1, wherein the imaging unit includes a cable over which the imaging unit receives and transmits control signals and image data representing the image of the region of interest from and to an external unit.

22. The system of claim 21, wherein the imaging unit further receives power from an external power unit through the cable.

23. The system of claim 1, wherein the endoscope includes a light post configured to be received by the light source assembly, the light post having a central longitudinal axis that is parallel to an optical axis of the system.

24. The system of claim 1 wherein the endoscope, the light source assembly, and the imaging unit are aligned along a central axis.

25. The system of claim 24 wherein the rotational joint allows the light source assembly and the endoscope to rotate together about the central axis while the imaging unit remains rotationally stationary about the central axis.

26. The system of claim 24 wherein the first coupling means comprises a snap-fit coupling.

27. An imaging system comprising:
an endoscope;
a light emitting diode (LED) assembly that provides light to be directed to a region of interest by the endoscope, wherein the LED assembly is coupled to the endoscope such that the endoscope is rotationally stationary with respect to the LED assembly and the endoscope is freely attachable to and detachable from the LED assembly;
an electronic control circuitry operatively coupled to the LED assembly that regulates output of the light provided by the LED assembly based on received control signals; and
an imaging unit comprising an image sensor, wherein the imaging unit is coupled to the LED assembly such that the LED assembly and the endoscope are able to rotate together while the imaging unit remains stationary and the LED assembly is freely attachable to and detachable from the imaging unit; and
wherein the LED assembly includes a rotational joint that allows the LED assembly and the endoscope to rotate together while the imaging unit remains stationary.

28. The imaging system of claim 27, wherein the electronic control circuitry regulates a drive current provided to the LED assembly to regulate an intensity of light emitted by the LED assembly responsive to a brightness of the region of interest detected by the image sensor.

29. The imaging system of claim 27, wherein the electronic control circuitry is configured to:
synchronize a duty cycle of the LED assembly with a frame clock of the image sensor; and
change the duty cycle of the LED assembly responsive to a brightness of the region of interest detected by the image sensor.

30. The system of claim 27 wherein the endoscope, the LED assembly, and the imaging unit are aligned along a central axis.

31. The system of claim 30 wherein the rotational joint allows the LED assembly and the endoscope to rotate together about the central axis while the imaging unit remains rotationally stationary about the central axis.

32. The system of claim 30 wherein the first coupling means comprises a snap-fit coupling.

33. A method comprising:
coupling an endoscope to a first coupling means that is coupled to a light source such that light provided by the light source is transmitted through the endoscope to a region of interest, the endoscope is rotationally stationary with respect to the light source assembly, and the endoscope is freely attachable to and detachable from the light source assembly,
coupling an imaging unit to a second coupling means that is coupled to the light source to form an endoscopic imaging system, the imaging unit being coupled to the light source such that an image formed by the endoscope is received by the imaging unit and the light source assembly is freely attachable to and detachable from the imaging unit,
wherein the light source assembly includes a rotational joint that allows the light source assembly and the endoscope to rotate together while the imaging unit remains stationary; and
coupling a power module to the endoscopic imaging system, the power module providing electrical power to the endoscopic imaging system.

34. The method of claim 33, wherein the light source comprises an LED assembly.

35. The method of claim 34 further comprising controlling a duty cycle of the LED assembly to regulate a light output responsive to a brightness of the region of interest received by the imaging unit.

36. The method of claim 34 further comprising regulating a drive current provided to the LED assembly to regulate an intensity of light emitted by the LED assembly responsive to a brightness of the region of interest received by the imaging unit.

37. The method of claim 33, wherein coupling the power module comprises coupling a power module that provides electrical power to the imaging unit and to the light source.

38. The method of claim 33, wherein coupling the imaging unit to the second coupling means that is coupled to the light source comprises coupling the imaging unit such that an electrical contact mechanism is coupled to the imaging unit and the light source, the electrical contact mechanism being connected to the power module to transmit electrical power provided by the power module to the light source.

39. The system of claim 33 wherein the endoscope, the light source assembly, and the imaging unit are aligned along a central axis.

40. The system of claim 39 wherein the rotational joint allows the light source assembly and the endoscope to rotate together about the central axis while the imaging unit remains rotationally stationary about the central axis.

41. The system of claim 39 wherein the first coupling means comprises a snap-fit coupling.

* * * * *